United States Patent [19]

Moriuma et al.

[11] Patent Number: 5,188,920
[45] Date of Patent: Feb. 23, 1993

[54] POSITIVE RESIST COMPOSITION CONTAINING 1,2-QUINONE DIAZIDE COMPOUND, ALKALI-SOLUBLE RESIN AND POLYHYDROXY PHENOL ADDITIVE COMPOUND

[75] Inventors: Hiroshi Moriuma, Nara; Haruyoshi Osaki, Toyonaka; Takeshi Hioki, Tondabayashi; Yasunori Uetani, Toyonaka, all of Japan

[73] Assignee: Sumitomo Chemical Company, Limited, Osaka, Japan

[21] Appl. No.: 712,729

[22] Filed: Jun. 10, 1991

[30] Foreign Application Priority Data

Jun. 14, 1990 [JP] Japan .................. 2-156877

[51] Int. Cl.$^5$ .................. G03F 7/023; G03C 1/61
[52] U.S. Cl. .................. 430/191; 430/165; 430/192; 430/193
[58] Field of Search ............ 430/191, 192, 193, 196

[56] References Cited

U.S. PATENT DOCUMENTS 4,059,449 11/1977 Rosenkranz et al.
4,594,306 6/1986 Stahlhofen et al. .......... 430/191
4,891,311 1/1990 Uenishi et al. ............. 430/193
5,112,719 5/1992 Yamada et al. ............. 430/191

FOREIGN PATENT DOCUMENTS 0150047 1/1984 Japan .................. 430/191

OTHER PUBLICATIONS

Patent Abstracts of Japan, vol. 14, No. 672 (P-1004) (4015) Feb. 9, 1990, JP-A-1 289 946 (Sumitomo Chem Co Ltd) Nov. 21, 1989, abstract only.

Primary Examiner—Charles L. Bowers, Jr.
Assistant Examiner—Christopher G. Young
Attorney, Agent, or Firm—Birch, Stewart, Kolasch & Birch

[57] ABSTRACT

A positive resist composition comprising a radiation-sensitive component and an alkali-soluble resin and a phenol compound of the formula:

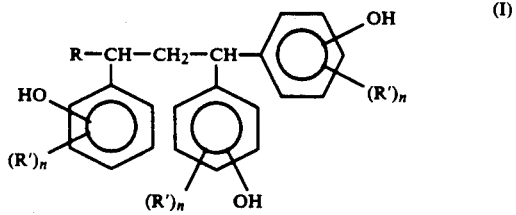

wherein R is a hydrogen atom, a lower alkyl group or a phenyl group, R' is an alkyl group or an alkoxy group, and n is a number of 0 to 3, which has well balanced good properties such as sensitivity, resolution, heat resistance and adhesiveness.

10 Claims, No Drawings

POSITIVE RESIST COMPOSITION CONTAINING 1,2-QUINONE DIAZIDE COMPOUND, ALKALI-SOLUBLE RESIN AND POLYHYDROXY PHENOL ADDITIVE COMPOUND

BACKGROUND OF THE INVENTION

Field of the Invention

The present invention relates to a resist composition which is sensitive to ultraviolet rays (G-line, H-line, I-line and so on), far ultraviolet rays (excimer laser and so on), electron rays, ion beam and radio-active rays, e.g. X rays.

Recently, particularly in the production of integrated circuits, miniaturization has proceeded as the integration level has increased, which results in demands for formation of patterns of submicron order and improved resolution. According to conventional processes for the production of integrated circuits, light exposure is accomplished by placing a mask in intimate contact to a substrate, e.g. a silicon wafer. It is said that this process cannot make patterns thinner than 2 $\mu$m. Instead of such conventional processes, the reduction projection exposure system attracts attention. According to this new system, a pattern of a master mask (reticle) is projected on the substrate with reduction by a lens system, whereby exposure is accomplished.

One of the serious problems in this system is low throughput. Namely, in this system, the total exposure time to expose a wafer is very long because of divided and repeated light exposure unlike a batch light exposure system which is employed in the conventional mask contact printing methods.

To solve this problem, not only an improvement in the apparatus but also an increase in sensitivity of the resist to be used are important. If the exposure time can be shortened by an increase in the sensitivity, the throughput and in turn the yield can be improved.

On the other hand, as the distance between the two adjacent lines is decreased with an increase in the integration level, dry etching with plasma and the like is also used together with wet etching. Due to the dry etching, the photoresist should have better resistance to dry etching (heat resistance) than ever. Since the wet etching is also used, the photoresist is required to have better resistance to wet etching (adhesiveness).

When the positive photoresist now in practical use is checked from this standpoint, its sensitivity, resolution and heat resistance are not necessarily satisfactory. Generally, the positive photoresist has lower sensitivity than the negative photoresist and improvement in the sensitivity of the former is desired.

To increase the sensitivity, it is easiest to decrease the molecular weight of an alkali-soluble resin used in the positive photoresist. The decrease of the alkali-soluble resin molecular weight accelerates dissolution of the photoresist in an alkaline developing solution so that the apparent sensitivity of the photoresist is increased.

This method, however, has a very serious disadvantage, namely, deterioration of the $\gamma$-value because of small difference of the dissolving rates in the developing solution between an exposed area and an unexposed area. Moreover, it encounters some problems such as decrease of heat resistance of the photoresist, large film thickness loss in an unexposed area (reduction of the so-called film thickness retention), a worsening of the shape of the pattern, etc.

Hitherto, positive resists satisfying desired sensitivity resolution, heat resistance and adhesiveness properties at the same time have not been on the market up to now. Attempts to improve one of these characteristics, leaves at least one of the remaining characteristics impaired.

SUMMARY OF THE INVENTION

One object of the present invention is to provide a positive resist composition which can overcome the above problems associated with the conventional positive resist compositions.

Another object of the present invention is to provide a positive resist composition which has well balanced properties such as sensitivity, resolution, heat resistance and adhesiveness.

Accordingly, the present invention provides a positive resist composition comprising a radiation-sensitive component and an alkali-soluble resin and a phenol compound of the formula:

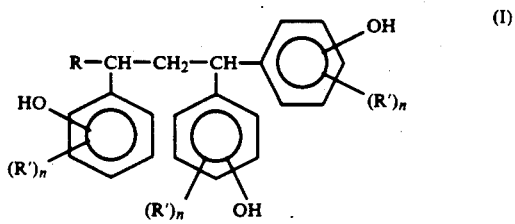

wherein R is a hydrogen atom, a lower alkyl group or a phenyl group, R' is an alkyl group or an alkoxy group, and n is a number of 0 to 3.

DETAILED DESCRIPTION OF THE INVENTION

In the formula (I), a lower alkyl group means an alkyl group having 1 to 3 carbon atoms.

In the formula (I), R' is preferably a $C_1$-$C_5$ alkyl group or alkoxy group (e.g. a methoxy group or an ethoxy group).

Among the compounds (I), preferred is a compound of the formula:

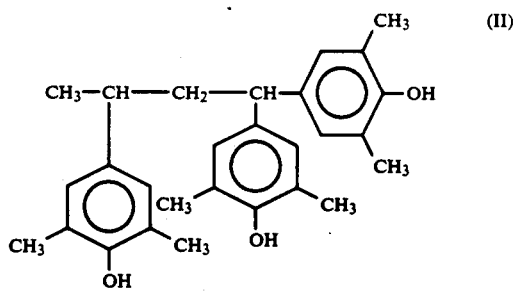

The phenol compound (I) may be prepared by reacting a phenol compound with an aldehyde compound of the formula:

wherein R is the same as defined above, in the presence of an acid catalyst.

The compound (II) can be prepared through a reaction of 2,6-xylenol and crotonaldehyde.

Examples of the phenol compound to be used in the above reaction are phenol, cresol, xylenol, 2,3,5-trimethylphenol, tert.-butylphenol, methoxyphenol, ethylphenol and the like.

Examples of the acid catalyst to be used in this condensation reaction include inorganic acids (e.g. hydrochloric acid, sulfuric acid, etc.) and organic acids (e.g. oxalic acid, p-toluenesulfonic acid, etc.).

An amount of the phenol compound is from 3 to 60 moles, preferably from 3 to 20 moles per one mole of the aldehyde compound.

An amount of the acid catalyst is preferably from 0.01 to 1.00 mole per one mole of the aldehyde compound.

A reaction temperature is usually from 50° to 110° C. and a reaction time is from 1 to 30 hours.

This reaction may be carried out in the presence or absence of a solvent.

Examples of the solvent to be used are water, alcohols (e.g. methanol, ethanol, isopropanol, n-butanol, isoamyl alcohol, etc.), ethylcellosolve acetate, ethylcellosolve, methylcellosolve, methyl isobutyl ketone, methyl ethyl ketone, hexane, heptane, benzene, toluene and so on.

An amount of the solvent is from 10 to 150 parts by weight per 100 parts by weight of the total amount of the phenol compound and the aldehyde compound.

After removal of the metal ions, the product is purified by washing it with a solvent or recrystallization.

One method for the removal of the metal ions is as follow:

The product is dissolved in an organic solvent which can be separated from a mixture with water, and washed with ion-exchanged water. Examples of such organic solvent include methyl isobutyl ketone, ethylcellosolve acetate, ethyl acetate and so on.

Another method for the removal of the metal ions is as follow:

The product is dissolved in an organic solvent which is not separated from a mixture with water, and charged into ion-exchanged water to precipitate the product. Examples of such organic solvent include methanol, ethanol, acetone and so on. This method is preferred, because the removal of the metal ions and purification of the condensation product are done at the same time.

An amount of the phenol compound (I) is from 4 to 40 parts by weight per 100 parts by weight of the total amount of the phenol compound (I) and the alkali-soluble resin.

When the amount of the phenol compound (I) is in the above range, development and patterning are easily done.

As the alkali-soluble resin, any of alkali-soluble resins which are used in the positive resist composition may be used. Preferred examples of the alkali-soluble resins are polyvinylphenol, a novolak resin and so on. The novolak resin is prepared by an addition condensation reaction of a phenol compound with an aldehyde. Specific examples of the phenol compound used as one of the raw materials for the synthesis of the novolak resin include phenol, o-cresol, m-cresol, p-cresol, 2,5-xylenol, 3,5-xylenol, 3,4-xylenol, 2,3,5-trimethylphenol, 4-tert.-butylphenol, 2-tert.-butylphenol, 3-tert.-butylphenol, 3-ethylphenol, 2-ethylphenol, 4-ethylphenol, 2-tert.-butyl-5-methylphenol, 2-tert.-butyl-6-methylphenol, 2-tert.-butyl-4-methylphenol, 2-naphthol, 1,3-dihydroxynaphthalene, 1,7-dihydroxynaphthalene, 1,5-dihydroxynaphthalene, etc. These phenols may be used alone or in combination.

The above condensation reaction is usually carried out at a temperature of 60° to 120° C. for 2 to 30 hours.

Examples of the acid catalyst used in this condensation reaction include organic and inorganic acids (e.g. oxalic acid, hydrochloric acid, sulfuric acid, perchloric acid, p-toluenesulfonic acid, trichloroacetic acid, phosphoric acid, formic acid, etc.) and salts with divalent metals (e.g. zinc acetate, magnesium acetate, etc.) and so on.

This reaction may be carried out in the presence or absence of a solvent.

Examples of the aldehyde is formaldehyde, paraformaldehyde, acetaldehyde, glyoxal, etc. In particular, 37 % formalin which is commercially mass produced is suitably used.

In particular, when the novolak resin is crystallized or fractionated after the condensation reaction and has, in a gel permeation chromatographic pattern (GPC pattern) measured by using a UV light (254 nm) detector, an area ratio of a range in which the molecular weight as converted to polystyrene is not larger than 900 does not exceed 25%, such resin is preferred.

As the radiation-sensitive component, a 1,2-quinone diazide compound is usually used in the positive resist composition of the present invention. Specific examples of the 1,2-quinone diazide compound are 1,2-benzoquinone diazide-4-sulfonic acid ester, 1,2-naphthoquinone diazide-4-sulfonic acid ester, 1,2-naphthoquinone diazide-5-sulfonic acid ester, etc.

Above esters may be prepared by per se conventional methods. For example, the ester is prepared by a condensation reaction of a compound having a hydroxyl group with 1,2-naphthoquinone diazide sulfonyl halide or benzoquinone diazide sulfonyl halide, preferably chloride, in the presence of a weak alkali.

Examples of the compound having a hydroxyl group are hydroquinone, resorcinol, phloroglucin, 2,4-dihydroxybenzophenone, trihydroxybenzophenones (e.g. 2,3,4-trihydroxybenzophenone, 2,2',3-trihydroxybenzophenone, 2,2',4-trihydroxybenzophenone, 2,2',5-trihydroxybenzophenone, 2,3,3'-trihydroxybenzophenone, 2,3,4'-trihydroxybenzophenone, 2,3',4-trihydroxybenzophenone, 2,3',5-trihydroxybenzophenone, 2,4,4'-trihydroxybenzophenone, 2,4',5-trihydroxybenzophenone, 2',3,4-trihydroxybenzophenone, 3,3',4-trihydroxybenzophenone, 3,4,4'-trihydroxybenzophenone, etc.); tetrahydroxybenzophenones (e.g. 2,3,3',4-tetrahydroxybenzophenone, 2,3,4,4'-tetrahydroxybenzophenone, 2,2',4,4'-tetrahydroxybenzophenone, 2,2',3,4-tetrahydroxybenzophenone, 2,2',3,4'-tetrahydroxybenzophenone, 2,2',5,5'-tetrahydroxybenzophenone, 2,3',4',5-tetrahydroxybenzophenone, 2,3',5,5'-tetrahydroxybenzophenone, etc.); pentahydroxybenzophenones (e.g. 2,2',3,4,4'-pentahydroxybenzophenone, 2,2',3,4,5'-pentahydroxybenzophenone, 2,2',3,3',4-pentahydroxybenzophenone, 2,3,3',4,5'-pentahydroxybenzophenone, etc.); hexahydroxybenzophenones (e.g. 2,3,3',4,4',5'-hexahydroxybenzophenone, 2,2',3,3',4,5'-hexahydroxybenzophenone; hydrofravan compounds of the formula:

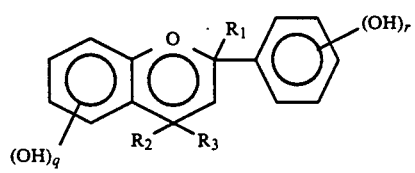

wherein q is a number of 0 to 4, r is a number of 1 to 5, and $R_1$, $R_2$ and $R_3$ are the same or different and respectively a hydrogen atom, an alkyl group, an alkenyl group, a cyclohexyl group or an aryl group; and alkyl gallates.

The positive resist composition of the present invention may contain two or more radiation-sensitive components in combination.

The positive resist composition of the present invention is prepared by mixing and dissolving the radiation-sensitive component, the alkali-soluble resin and the phenol compound (I) in a solvent.

An amount of the radiation-sensitive component is from 5 to 100 parts by weight, preferably 10 to 50 parts by weight per 100 parts by weight of a total amount of the phenol compound (I) and the alkali-soluble resin.

When the amount of the radiation-sensitive component is 5 to 100 parts by weight, it is easy to make the pattern, and the positive resist composition has excellent sensitivity.

Preferably, the used solvent evaporates at a suitable drying rate to give a uniform and smooth coating film. Such a solvent includes ethylcellosolve acetate, methylcellosolve acetate, ethylcellosolve, methylcellosolve, propyleneglycol monomethyl ether acetate, butyl acetate, methyl isobutyl ketone, xylene, ethyl lactate, propyleneglycol monoethylether acetate, etc.

An amount of the solvent is 30 to 80% by weight of the resist composition when ethylcellosolve acetate is used as the solvent.

To the positive photoresist composition obtained by the foregoing method, small amounts of resins, dyes, etc. may be added if desired.

The resist composition of the present invention has better sensitivity than the conventional resist compositions and improved resolution and heat resistance.

PREFERRED EMBODIMENTS OF THE INVENTION

The present invention will be illustrated more in detail with the following Examples, but it is not limited to these Examples. In Examples, "parts" are by weight unless otherwise indicated.

SYNTHETIC EXAMPLE 1

Into a three-necked 1000 ml flask equipped with a stirrer, a condenser and a thermometer 2,6-xylenol (610.9 g), crotonaldehyde (17.5 g), toluene (305.5 g) and p-toluenesulfonic acid (2.5 g) were charged and reacted on an oil bath at 100° to 105° C. for 25 hours while stirring. Then, the mixture was cooled to room temperature and filtered. The product was recrystallized from toluene to obtain a compound of the formula:

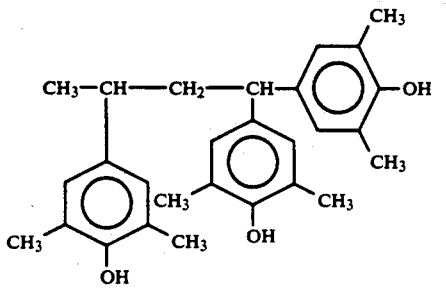
(II)

SYNTHETIC EXAMPLE 2

Into a four-necked 500 ml flask equipped with a stirrer, a condenser, a dropping funnel and a thermometer 2,5-xylenol (347.3 g), methanol (300 g) and 36% hydrochloric acid (223 g) were charged. To the mixture, crotonaldehyde (66.4 g) was dropwise added at 65° C. over 2 hours. After the addition of crotonaldehyde, the mixture was reacted at 65° to 75° C. for 5 hours. Then, the reaction mixture was cooled to room temperature and filtered. The product was washed with toluene and dried to obtain a compound of the formula:

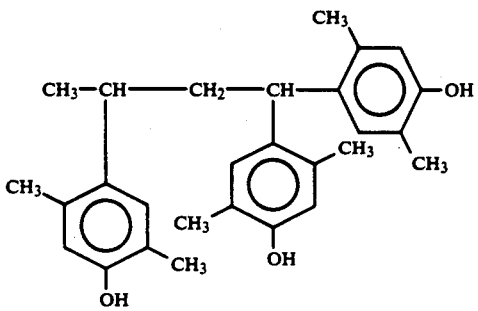

SYNTHETIC EXAMPLE 3

Into a three-necked 1000 ml flask, m-cresol (129.6 g), p-cresol (194.4 g), ethylcellosolve acetate (302.4 g) and 5% oxalic acid (36.5 g) were charged. To the mixture heated on an oil bath at 80° C., 37% formalin (182.4 g) was dropwise added over 60 minutes, followed by further stirring for 7 hours while heating. Then, the reaction mixture was neutralized, washed with water and dehydrated to obtain a solution of a novolak resin in ethylcellosolve acetate. A weight average molecular weight measured by GPC was 3710 as converted to polystyrene.

SYNTHETIC EXAMPLE 4

The solution of the novolak resin in ethylcellosolve acetate obtained in Synthetic Example 3 (a content of the novolak resin being 34.1%) (120 g) was poured in a 3 liters separable flask having an outlet at its bottom. Thereto, ethylcellosolve acetate (425.8 g) and n-heptane (292.7 g) were added, and the mixture was stirred at 20° C. for 30 minutes, kept standing and separated.

From the lower layer obtained by separation, n-heptane was evaporated off by an evaporator to obtain a solution of a novolak resin in ethylcellosolve acetate. A weight average molecular weight measured by GPC was 7440 as converted to polystyrene.

EXAMPLES 1, 2 and 3

The condensate obtained in Synthetic Example 1 and the resins obtained in Synthetic Examples 3 and 4 was dissolved together with a radiation-sensitive component in amounts in the Table to prepare a resist solution. The amount of the solvent was adjusted to form a film having a thickness of 1.28 μm when the resist solution was applied under the coating conditions below.

Each composition was filtered through a Teflon (trade of 0.2 μm in pore size to prepare a resist solution. The solution was then coated on a silicon wafer, which had been rinsed in a usual manner, by means of a spinner to a thickness of 1.28 μm. The coated silicon wafer was baked for 60 seconds on a hot plate kept at 100° C. and exposed to light the exposure time of which was varied stepwise at each shot by means of a reduction projection exposure apparatus (NSR 1505 G3C manufactured by Nikon Corporation, NA=0.42) with a light having a wavelength of 436 nm (g line). Then, the wafer was developed for one minute in a developer (SOPD (trade name) manufactured by Sumitomo Chemical Company, Limited) to obtain a positive pattern.

After rinsing and drying, the amount of film thickness loss for each shot was plotted against the exposure time to calculate sensitivity. The film thickness retention was calculated from the remaining film thickness in the unexposed area.

Also, the silicon wafer having a resist pattern was placed for 3 minutes in a direct hot plate at various temperatures in air, and the heat resistance was evaluated by observing thermal deformation of the 3 μm line-and-space pattern by means of a scanning electron microscope.

COMPARATIVE EXAMPLES 1 AND 2

In the same manner as in Example 1 but dissolving the resin obtained in Synthetic Example 3 or 4 together with the radiation-sensitive component in amounts shown in the Table, the resist composition was prepared, exposed and developed. In the same manners as in Example 1, the sensitivity and the film thickness retention were calculated, and the heat resistance was evaluated.

The results are shown in the following Table, in which "parts" are by weight.

TABLE

| Example No. | 1 | 2 | 3 | C. 1 | C. 2 |
|---|---|---|---|---|---|
| Amount of phenol compound obtained in Syn. Ex. 1 (parts) | 3.5 | 3.5 | 3.5 | — | — |
| Kind of novolak resin (Syn. Ex. No.) | No. 3 | No. 4 | No. 4 | No. 3 | No. 4 |
| Amount (parts) | 13.5 | 13.5 | 13.5 | 17 | 17 |
| Kind[1] of radiation-sensitive component | (1) | (1) | (2) | (1) | (1) |
| Amount (parts) | 4.8 | 4.8 | 4.0 | 4.8 | 4.8 |
| Sensitivity[2] (msec.) | 120 | 223 | 343 | 172 | 850 |
| Film thickness retention (%) | 96.6 | 98.7 | 98.0 | 92.8 | 99.4 |
| Heat resistance[3] (°C.) | 130 | 160 | 160 | 120 | 150 |
| Resolution (μm) | 0.70 | 0.55 | 0.55 | 0.80 | 0.90 |

Note:
[1] Radiation-sensitive component
(1) A condensation product of naphthoquinone-(1,2)-diazide-(2)-5-sulfonyl chloride with 2,3,4,4'-tetrahydroxybenzophenone (2.5 hydroxy groups are esterified on the average).
(2) A condensation product of naphthoquinone-(1,2)-diazide-(2)-5-sulfonyl chloride with a compound of the formula:

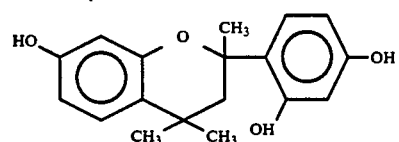

[2] The minimum exposing time (msec) at which the resist film thickness becomes 0 (zero).
[3] A temperature at which the 3 μm line-and-space pattern begins to thermally deform.

What is claimed is:

1. A radiation-sensitive positive resist composition comprising, in admixture, a 1,2-quinone diazide compound, an alkali-soluble resin and a phenol compound of the formula:

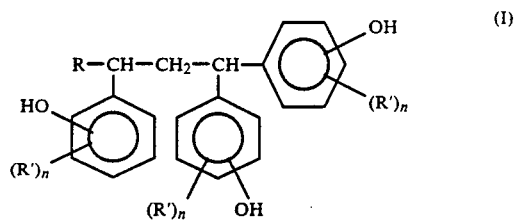

wherein R is a hydrogen atom, a lower alkyl group or a phenyl group, R' is an alkyl group or an alkoxy group, and n is a number of 0 to 3, wherein an amount of said 1,2-quinone diazide compound and an amount of said phenol compound are from 5 to 100 parts by weight and from 4 to 40 parts by weight, respectively, per 100 parts by weight of a total amount of said phenol compound and said alkali-soluble resin.

2. The radiation-sensitive positive resist composition according to claim 1, wherein R is a $C_1$–$C_3$ alkyl group.

3. The radiation-sensitive positive resist composition according to claim 1, wherein R' is a $C_1$–$C_5$ alkyl group or an alkoxy group.

4. The radiation-sensitive positive resist composition according to claim 1, wherein R is a hydrogen atom, a $C_1$–$C_3$ alkyl group or a phenyl group, and R' is a $C_1$–$C_5$ alkyl group or an alkoxy group.

5. The radiation-sensitive positive resist composition according to claim 1, wherein said alkali-soluble resin is a polyvinylphenol or novolak resin.

6. The radiation-sensitive positive resist composition according to claim 1, wherein said alkali-soluble resin is a novolak resin which is characterized in that an area ratio in GPC of a range in which the molecular weight as converted to polystyrene is not larger than 900 does not exceed 25%.

7. The radiation-sensitive positive resist composition according to claim 1, wherein said 1,2-quinone diazide compound is selected from the group consisting of 1,2-benzoquinone diazide-4-sulfonic acid ester, 12,-naphthoquinone diazide-4-sulfonic acid ester, and 1,2-naphthoquinone diazide-5-sulfonic acid ester.

8. The radiation-sensitive positive resist composition according to claim 1, wherein the 1,2-quinone diazide compound is present in an amount of from 10 to 50 parts by weight per 100 parts by weight of the total amount of said phenol compound and said alkali-soluble resin.

9. The radiation-sensitive positive resist composition according to claim 1, wherein said phenol compound is a compound of the formula:

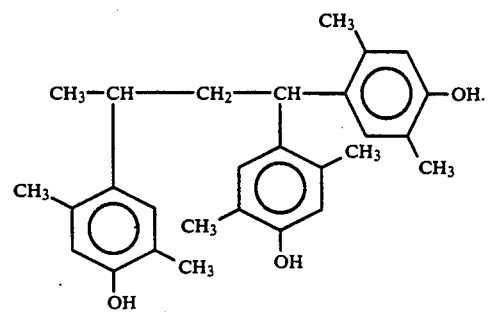

10. The radiation-sensitive positive resist composition according to claim 1, wherein said phenol compound is a compound of the formula:

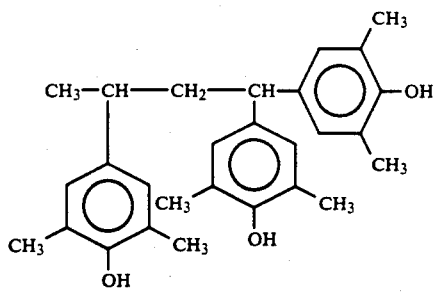
(II)